US010426977B2

(12) United States Patent
Stacey et al.

(10) Patent No.: US 10,426,977 B2
(45) Date of Patent: Oct. 1, 2019

(54) MOVING FLOOR FOR RADIOTHERAPY SYSTEM WITH CANTILEVER GANTRY ASSEMBLY

(71) Applicant: Varian Medical Systems Particle Therapy GmbH, Troisdorf (DE)

(72) Inventors: Gary Stacey, Cambridge (GB); Congyi Huang, Cambridge (GB); Alexander Norman, Cambridge (GB); Mark Rogers, Cambridgeshire (GB)

(73) Assignee: VARIAN MEDICAL SYSTEMS PARTICLE THERAPY GMBH., Troisdorf (DE)

( * ) Notice: Subject to any disclaimer, the term of this patent is extended or adjusted under 35 U.S.C. 154(b) by 27 days.

(21) Appl. No.: 15/639,993

(22) Filed: Jun. 30, 2017

(65) Prior Publication Data

US 2019/0001157 A1    Jan. 3, 2019

(51) Int. Cl.
*A61N 5/10* (2006.01)

(52) U.S. Cl.
CPC .......... *A61N 5/1081* (2013.01); *A61N 5/1043* (2013.01); *A61N 5/1049* (2013.01); *A61N 2005/1061* (2013.01); *A61N 2005/1087* (2013.01)

(58) Field of Classification Search
CPC ... A61N 5/1049; A61N 5/1081; A61B 6/0471
See application file for complete search history.

(56) References Cited

U.S. PATENT DOCUMENTS

| | | | |
|---|---|---|---|
| 8,368,043 B2* | 2/2013 | Havelange | A61N 5/1081 250/454.11 |
| 8,975,602 B2* | 3/2015 | Huber | A61N 5/1081 250/396 R |
| 2004/0061078 A1* | 4/2004 | Muramatsu | A61N 5/10 250/492.3 |
| 2004/0111134 A1* | 6/2004 | Muramatsu | A61N 5/10 607/88 |
| 2005/0161618 A1 | 7/2005 | Pedroni | |
| 2007/0217575 A1* | 9/2007 | Kaiser | A61N 5/10 378/209 |

(Continued)

FOREIGN PATENT DOCUMENTS

| | | |
|---|---|---|
| EP | 2308561 | 4/2011 |
| JP | S5675174 | 6/1981 |

(Continued)

*Primary Examiner* — Wyatt A Stoffa (57) ABSTRACT

A proton beam therapy system with a cantilever gantry system and a moving floor system. The moving floor system includes a flexible moving floor and a track that is disposed vertically and affixed to an external wall. The track includes a lateral portion providing a linear lateral path for the part of the moving floor and non-lateral portions providing a vertical path for the excess of the floor. The non-lateral portions may be located above or below the lateral portion. During rotation of the cantilever gantry and when the beam nozzle is positioned under the patient table, an opening is maintained in the floor through which the beam nozzle protrudes. The opening follows the changing positions of the beam nozzle and moves in the floor plane in synchronization with the rotation of the gantry.

7 Claims, 11 Drawing Sheets

(56) References Cited

U.S. PATENT DOCUMENTS

| | | | |
|---|---|---|---|
| 2008/0029706 A1* | 2/2008 | Kaiser | A61N 5/10 250/363.02 |
| 2008/0189859 A1* | 8/2008 | Sloan | A61N 5/10 5/601 |
| 2008/0219407 A1* | 9/2008 | Kaiser | A61N 5/10 378/65 |
| 2011/0299657 A1* | 12/2011 | Havelange | A61N 5/1081 378/65 |
| 2014/0121441 A1* | 5/2014 | Huber | A61N 5/1081 600/1 |
| 2017/0001041 A1* | 1/2017 | Yamashita | A61N 5/1049 |
| 2017/0340903 A1* | 11/2017 | Ie | A61B 6/032 |
| 2018/0028835 A1 | 2/2018 | Bennett et al. | |
| 2018/0028838 A1* | 2/2018 | Spotts | G21K 1/10 |
| 2018/0064958 A1* | 3/2018 | Kobayashi | A61N 5/1081 |

FOREIGN PATENT DOCUMENTS

| | | |
|---|---|---|
| JP | S62183775 | 8/1987 |
| JP | 2011250910 | 12/2011 |
| WO | WO2011053960 | 5/2011 |
| WO | WO2013093020 | 6/2013 |
| WO | WO2014041003 | 3/2014 |
| WO | WO2015042535 | 3/2015 |

* cited by examiner

MOVING FLOOR FOR RADIOTHERAPY SYSTEM WITH CANTILEVER GANTRY ASSEMBLY

CROSS REFERENCE TO RELATED APPLICATION

This application is related to the co-pending commonly-assigned U.S. patent application Ser. No. 15/458,780, filed on Mar. 14, 2017, entitled "ROTATABLE CANTILEVER GANTRY IN RADIOTHERAPY SYSTEM," the entire content of which is herein incorporated by reference for all purposes.

TECHNICAL FIELD

The present disclosure relates generally to the field of radiation therapy systems, and, more specifically, to treatment station floor configurations for radiation therapy systems.

BACKGROUND OF THE INVENTION

In a typical proton therapy system used for tumor radiation treatment for example, a proton beam is generated and output from an accelerator, e.g., a cyclotron or a synchrotron, with a certain initial energy. The initial energy determines a maximum penetration depth of the proton beam and typically is 250 MeV. As the proton beam travels through a beam transportation system or a beamline, the beam energy is precisely tuned through energy selection mechanisms, e.g., an energy degrader or energy slit. The beam transport system includes a plurality of magnets for beam redirection (bending), focusing and steering. A rotational gantry with a radiation nozzle (or beam nozzle) is located at the end of the beam transport system. Eventually, the beam is delivered to a treatment station and irradiated onto a patient at an energy level prescribed for the specific treatment session based on the tumor volume, geometry, location etc.

Due to the extremely high cost of purchasing and maintaining such a radiation system, a medical facility usually uses one accelerator for a plurality of treatment stations so the high expenditure for the accelerator facilities is distributed. Although using a multi-station single-cyclotron system is effective to distribute the cost for large medical facilities, the overall cost of such a multi-gantry system can be prohibitively high for smaller facilities that may only need one treatment station. Also, some multi-station systems do not support simultaneous treatment in multiple stations. This contribute to further disadvantage that a delay at one treatment station can cause delay at the other station.

With the demand for proton beam radiation therapy rising worldwide, smaller and less expensive proton therapy systems are highly desired to increase patient access to therapy. In a proton radiation system, a gantry system alone typically weighs over 200 tons which is mainly contributed by the massive magnets installed in the gantry. To support and precisely control the motion of such a large weight, existing rotatable gantries are supported by a front and a rear ring structures, between which the components in the gantry beamline are suspended. That is, the gantry is supported in a simply-supported manner, in that the weight of the gantry is supported at both end portions of the gantry.

Typically, the front and rear rings are respectively coupled to front and rear rollers that can rotate with the gantry. The rings and rollers are affixed to the ground through fixtures which are made of steel and concrete. The two rings, plus the additional structural members to stiffen the assembly, make the gantry system appear to be a tremendously large and heavy conical (generally tapering from right to left as illustrated) or cylindrical drum-shaped structure in a treatment station. This structure defines the overall size of the gantry, such as the end-to-end gantry length. It also undesirably limits patient positioning and makes it difficult to make incremental improvements to the beam optics geometry because the critical dimensions are determined by the mechanical structure, not by the magnet positioning.

More importantly, using two rollers to support introduces random deflection errors during rotation due to the inherent difficulty in aligning the two rollers perfectly. As a result, the gantry tends to precess, causing the beam spot location to shift in an unpredictable manner. In practice, remarkable time and resources are often spent on realigning and repositioning the rollers in the attempt to fix the random errors and maintain beam precision.

Moreover, a typically rotatable gantry is capable of rotating in a range greater than 180° such that the beam nozzle can irradiate toward a patient in various prescribed angles, e.g., both from above the patient table and from underneath the patient table. It is desirable that the floor in the treatment station can safely support a clinician's access to the gantry and the patient table for treatment preparation without interfering with gantry movement during treatment.

SUMMARY OF THE INVENTION

Accordingly, disclosed herein provide a proton therapy system having a compact and lightweight gantry assembly and an actively moving floor operable to maintain an opening through which the beam nozzle can irradiate toward the back side of the patient table. The opening can move along a linear path in synchronization with rotation of the gantry assembly.

Embodiments of the present disclosure include a gantry that is configured as an open-ended cantilever arm with one end portion (the fixed end portion) affixed to an external structure that supports the weight of the gantry. The remainder of the gantry is cantilevered and the free end portion coupled to a beam nozzle. A main bearing is coupled to the fixed end portion and enables the gantry to rotate in a full range of 360° (or more) around the iso-center. A large counterweight can be disposed in the fixed end portion to keep the system center of mass close to the bearing. The housing of the gantry may be composed of one or more monocoque sections, for example, a cantilever section carrying or enclosing the magnets and other components of the gantry beamline and a drum section on which the bearing is placed.

According to the present disclosure, the weight of a proton beam gantry is supported in a cantilevered manner at one location, e.g., through a main bearing. Compared with the simply-supported gantries in the conventional proton beam therapy systems, a cantilever gantry advantageously eliminates the need for a roller or a bearing or other support structure around the treatment area and thereby removes a major source of random deflection errors. The cantilevered design is de-coupled from the gantry rotating mechanism, advantageously allowing the beam geometry to be modified without significantly changing the rotating bearing structure. Further, with the simplified supporting mechanism, a cantilever gantry can be made compact and lightweight, allowing significantly improved flexibility in the positioning of a patient while maintaining the full range rotation capacity of the gantry. Moreover, by using monocoque housing, a gantry according to the present disclosures can be delivered to a healthcare facility as a fully-assembled and pre-tested unit. Consequently, the expenditure associated with manufacture, transportation, installation, assembly and maintenance can be dramatically and advantageously decreased.

The floor system used in conjunction with such a cantilever gantry includes a flexible moving floor and a vertical track that is affixed to an external wall. The flexible moving floor may be composed of a plurality of segments linked in sequence and coupled to the track through bogies. The track includes: a lateral portion that guides the moving floor to move in the floor plane; and non-lateral portions that extend from ends of the lateral portion and guide the moving floor to move away from the floor plane. The non-lateral portions may be located above the floor plane and thus guide the excess of the flexible moving floor upward. Alternatively, the non-lateral portions may be located below the floor plane and thus guide the excess downward.

During rotation of the gantry, when the beam nozzle is positioned above the patient table, the moving floor moves and maintains a continuous surface; when the beam nozzle is positioned under the patient table, an opening is maintained in the moving floor through which the beam nozzle protrudes and toward the target region of the patient. The opening follows the changing positions of the beam nozzle and moves in the floor plane in synchronization with the rotation of the gantry. In some embodiments, the moving floor may be composed of a single train of segments and the opening is formed by opposite ends of the trains. In some other embodiments, the moving floor may be composed of two trains that are independently driven, and the opening corresponds to the gap between ends of the two trains.

A moving floor system according to the present disclosure provides a safe surface for clinicians to stand on during treatment preparation and maintenance. The flexible moving floor advantageously covers all gaps and hides the unwanted view of the gantry pit from the treatment station. It also advantageously permits full range rotation of the gantry and beam nozzle by moving out of the way for the nozzle to pass and irradiating toward a patient underneath the patient table.

BRIEF DESCRIPTION OF THE DRAWINGS

Embodiments of the present invention will be better understood from a reading of the following detailed description, taken in conjunction with the accompanying drawing figures in which like reference characters designate like elements and in which.

DETAILED DESCRIPTION

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention.

Although a method may be depicted as a sequence of numbered steps for clarity, the numbering does not necessarily dictate the order of the steps. It should be understood that some of the steps may be skipped, performed in parallel, or performed without the requirement of maintaining a strict order of sequence. The drawings showing embodiments of the invention are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the invention can be operated in any orientation.

Moving Floor for Radiotherapy System with
Cantilever Gantry Assembly

Overall, embodiments of the present disclosure provide a radiotherapy system including a rotatable gantry with its weight supported in a cantilevered manner. The fixed end portion of the cantilever gantry has a main bearing enabling the gantry to rotate in 360° around an iso-center. The open end portion of the cantilever gantry is suspended and coupled to a beam nozzle used to irradiate a particle beam onto a patient positioned according to the iso-center.

Moreover, a moving floor system is used in conjunction with a cantilever gantry, which includes a flexible moving floor and a vertical track affixed to an external wall. The track includes a lateral portion providing a linear lateral path for the part of the moving floor that moves across the treatment station, and non-lateral portions providing an approximately vertical path for the excess of the moving floor (or floor excess). In some embodiments, the non-lateral portions may be located above the lateral portion so that the excess of the moving floor to roll up. In some other embodiments, the non-lateral portions may be located below the lateral portion so that the excess of the moving floor to roll down.

During rotation of the cantilever gantry and viewed in the treatment station, when the beam nozzle is positioned above the patient table, the floor moves and maintains a continuous surface; when the beam nozzle is positioned under the patient table, an opening is maintained in the floor through which the beam nozzle protrudes. The opening follows the changing positions of the beam nozzle and moves in the floor plane in synchronization with the rotation of the gantry.

Figure 1A:
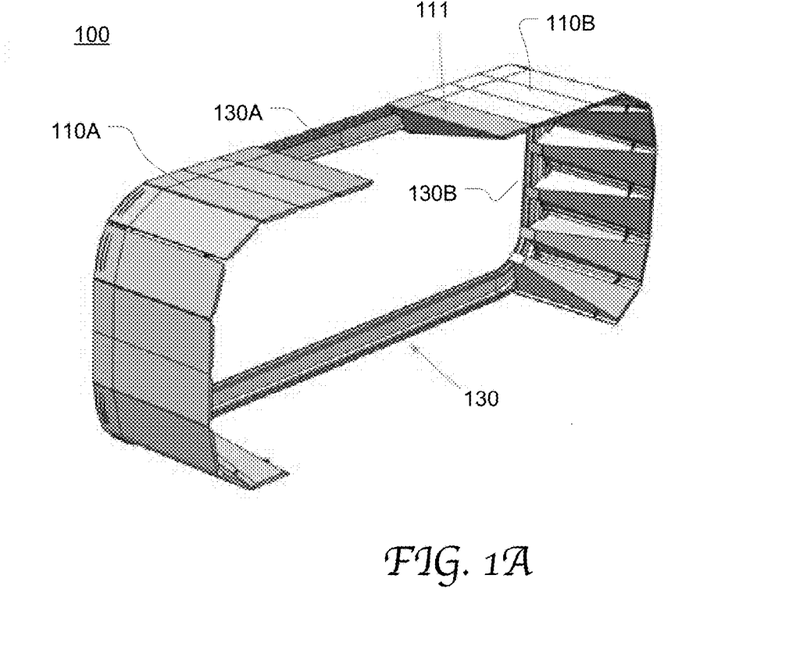
FIG. 1A illustrates the configuration of an exemplary floor system in a proton beam therapy system with the floor excess rolling downward according to a first embodiment of the present disclosure.
Figure 1B:
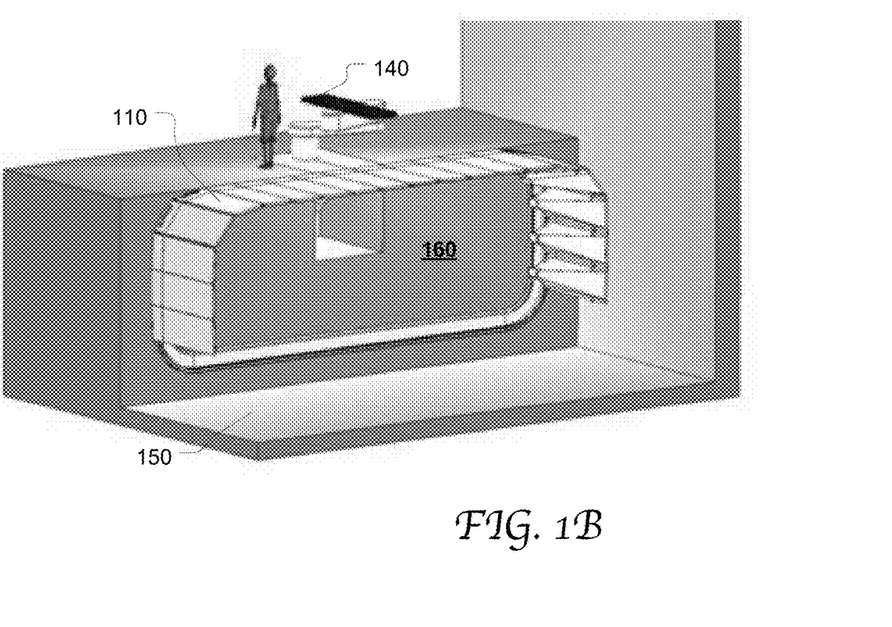
FIG. 1B illustrates the exemplary moving floor system installed on the bunker wall according to the first embodiment of the present disclosure.

FIG. 1A illustrates the configuration of an exemplary moving floor system 100 used in a proton beam therapy system with the floor excess rolling downward according to a first embodiment of the present disclosure. FIG. 1B illustrates the exemplary moving floor system 100 installed on the building wall, e.g., the treatment station bunker wall 160. The flexible floor 110 composed of two trains 110A and 110B of several floor segments can run along the single track 130. As described in greater detail below, each floor segment (e.g., 111) is mounted on the track 130 on only one side and thus supported in a cantilevered manner. In this example, the track 130 is approximately a square continuous loop. However, it will be appreciated that the track can be configured in any other suitable geometry without departing from the scope of the present disclosure. For example, the track may be open ended in some other embodiments.

During system off time, the two floor trains 110A and 110B provide a stationary and continuous floor on which a clinician can stand, as shown in FIG. 1B. Similarly, during operation while the gantry rotates in a range that requires no interplay between the gantry and the floor, the ends of the two floor trains 110A and 110B meet and present a continuous floor to cover the bunker pit 150 that otherwise would be undesirably exposed to a patient. In this situation, the flexible floor 110 may remain stationary or move along the track 130 while maintaining a continuous surface.

Figure 2:
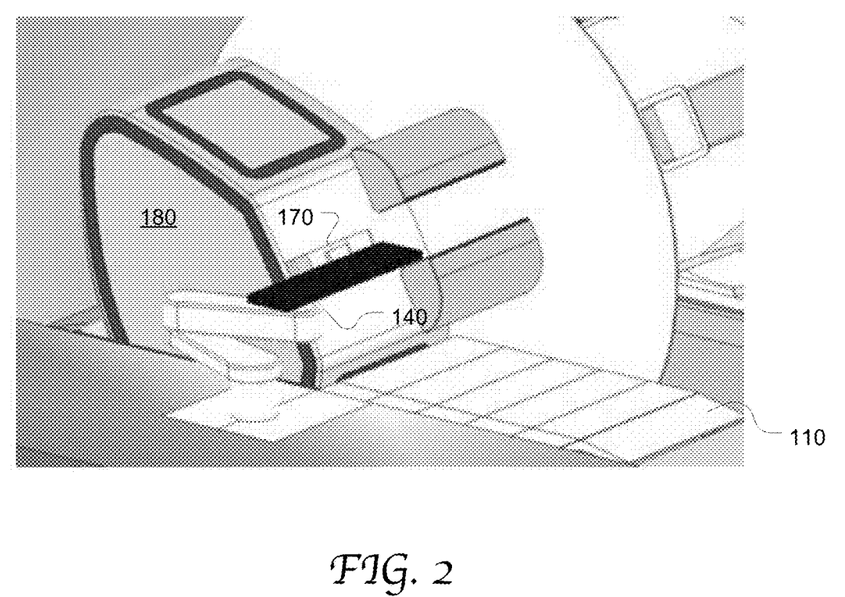
FIG. 2 illustrates a state that the floor opening allows the gantry and beam nozzle to rotate to below the floor level according to the first embodiment of the present disclosure.

When the gantry rotates in a range where at least a portion of the gantry is below the floor plane, the two floor trains 110A and 110B are separated to create an opening in the floor for the beam nozzle to pass through. This advantageously allows the beam nozzle to irradiate onto a patient from below the patient table 140 as well as from the side thereof. FIG. 2 illustrates a state that the floor opens for the gantry 160 and beam nozzle 170 to rotate to below the floor plane according to the first embodiment of the present disclosure. The present disclosure is not limited to any specific angular position of the gantry from which the floor starts to open and allows the gantry to enter. Such angular position varies in different embodiments and is determined by the particular physical configurations of the gantry and the nozzle.

As the gantry rotates further under the floor plane, the opening consistently follows the varying position of the beam nozzle. Further, the dimension of the opening may dynamically vary with position of the beam nozzle. As a result, the beam nozzle and the floor trains 110A and 110B in combination can form an effective moving cover of the bunker pit 150. It will be appreciated that the present disclosure is not limited by the particular portion of the beam nozzle and/or gantry that can protrude above the opening.

Referring FIG. 1A, in this embodiment, the non-lateral portions 130B of the track 130 are substantially vertical and bent downward from the ends of the top lateral portion 130A. Thus, the excess segments can roll along the non-lateral portions 130B and thus are invisible in the treatment area.

The two floor trains 110A and 110B may be independently driven by separate motors and coupled to separate brakes, allowing them to travel along the track 130 at different speeds and in different directions. The motors are controlled to enable the floor trains 110A and 110B to move in synchrony with gantry rotation and thereby to dynamically adjust the dimension and position of the opening for the beam nozzle to pass through. However, in some other embodiments, the floor trains 110A and 110B may be passively driven by motion of the gantry and the beam nozzle. In a floor failure scenario, the floor trains 110A and 110B may be moved out of the way and the gantry may still rotate, so treatment may still continue.

Figure 3A:
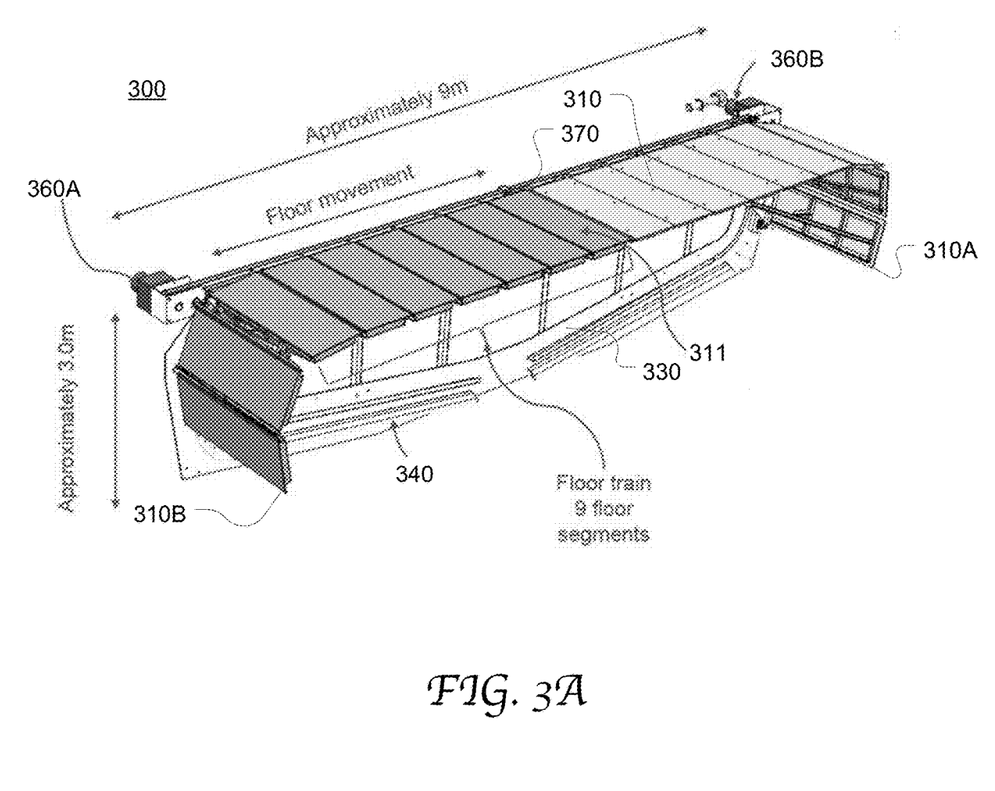
FIG. 3A illustrates the configuration of an exemplary moving floor system that can be implemented as a chassis-based pre-assembled module according to the second embodiment of the present disclosure.

In the first embodiment as described above, the track 130 may be directly mounted on the concrete of the bunker wall 160. However, in some other embodiments, the track and the floor trains can be mounted to a steel chassis plate, advantageously enabling the entire floor system to be a standalone pre-assembled module. Such a floor module can be fully tested independently of the gantry and may have adjustment features that allow fast and efficient installation without manufacture of shims. This advantageously allows quick and efficient installation on-site. FIG. 3A illustrates the configuration of an exemplary moving floor system 300 that can be implemented as a chassis-based pre-assembled module according to the second embodiment of the present disclosure.

In this embodiment, the track 330 and floor trains 310A and 310B are integrated on steel chassis plate 340 which is mounted to the concrete structure of the building. Each floor train includes, 9 segments e.g., 311 that are cantilevered from the chassis. For instance, the total length of the lateral portion of the track 330 is approximately 9.0 m, which corresponds to the treatment room width. The floor trains 310A and 310B are connected to the drive motors 360A and 360B respectively, for instance via a toothed belt 370. The floor trains 310A and 310B move along the same rail (320 in FIG. 3B) of the track and yet their motion is independent of each other.

Figures 3B, 3C:
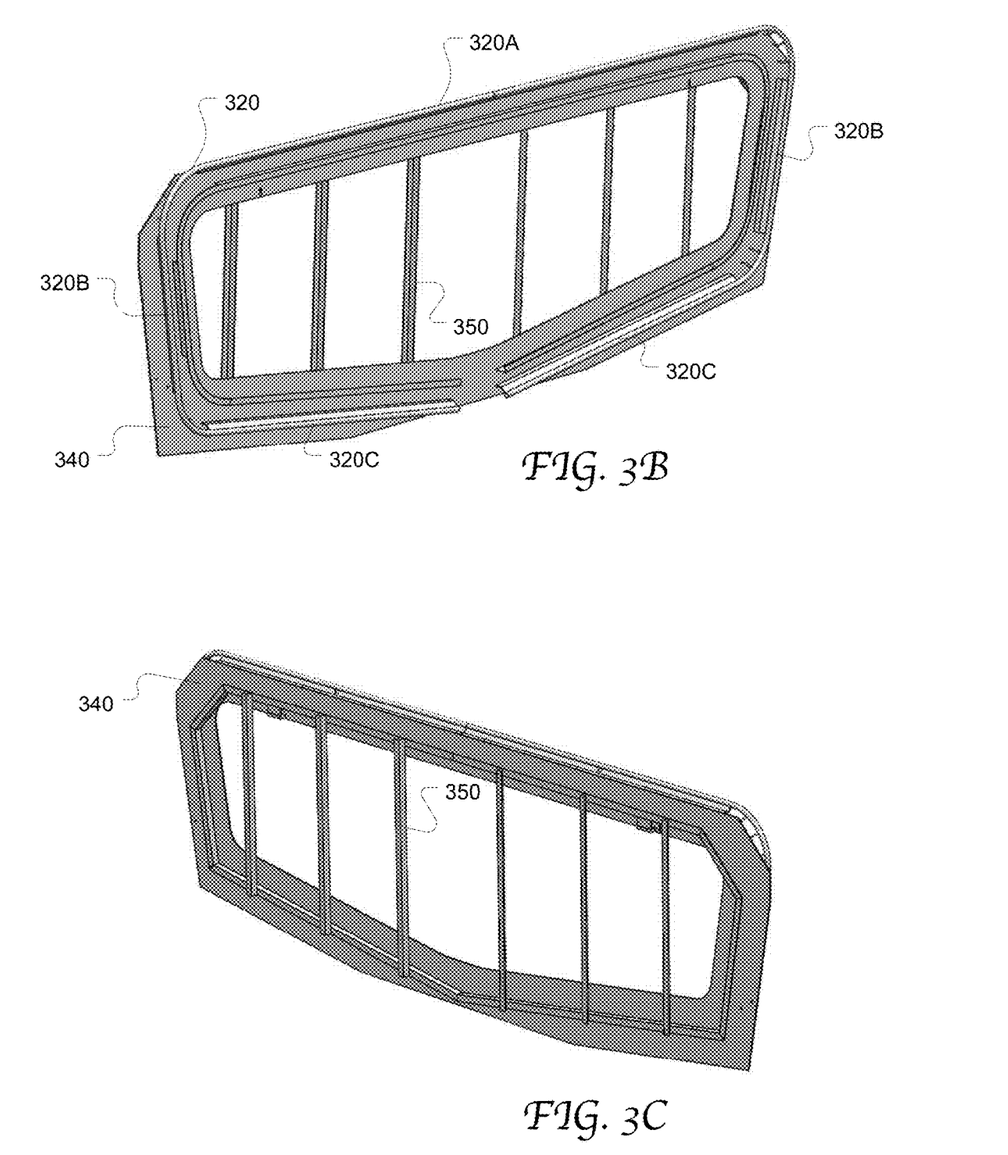
FIG. 3B illustrates a front (gantry-facing) view of the exemplary chassis according to the second embodiment of the present disclosure.
FIG. 3C illustrates a rear view of the exemplary chassis according to the second embodiment of the present disclosure.

FIG. 3B illustrates a front view of the exemplary chassis plate 340 according to the second embodiment of the present disclosure as shown in FIG. 3A. FIG. 3C illustrates a rear view of the exemplary chassis 340. The chassis is approximately 3.0 m high and has a welded fabrication. The rail 320 may be a tubular structure that is routed around the edges of the chassis plate 340 and spaced off the chassis plate 340.

As shown in FIGS. 3B and 3C, the rail 320 includes a top lateral portion 320A, two approximately vertical portions 320B and two bottom portions 320C. The bottom sections 320C are angled, rather than flat, which can help the floor trains (310A and 310B in FIG. 3A) to clear the second dipole (e.g., 712 in FIG. 7) when the floor is fully open, so that the full range of treatment can proceed despite an unexpected floor failure. Further, even if a floor train is driven from the top end, the entire floor train is constantly in tension, which can advantageously reduce the chance of floor jamming. The chassis plate 340 may be stiffened on the rear with angle steel sections. This stiffening follows the paths of the rail with the addition of vertical stiffeners 350.

The vertical portions 320B of the rail may not be perfectly perpendicular to the floor plane. This can advantageously prevent the floor segments from flapping frequently and noisily left and right due to clearance in the bearings as they move up and down. The angle from the vertical orientation advantageously biases the floor segments to a specified side, so they only tip over once.

Figure 4:
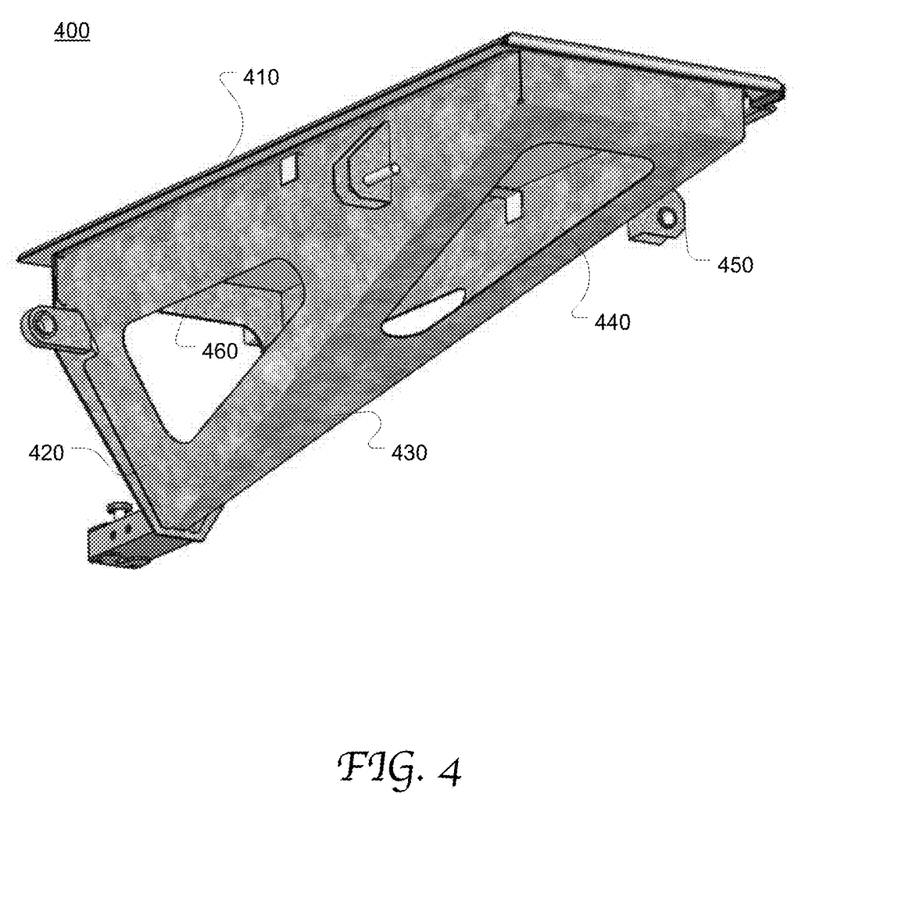
FIG. 4 illustrates an exemplary floor segment according to an embodiment of the present disclosure.
Figure 5:
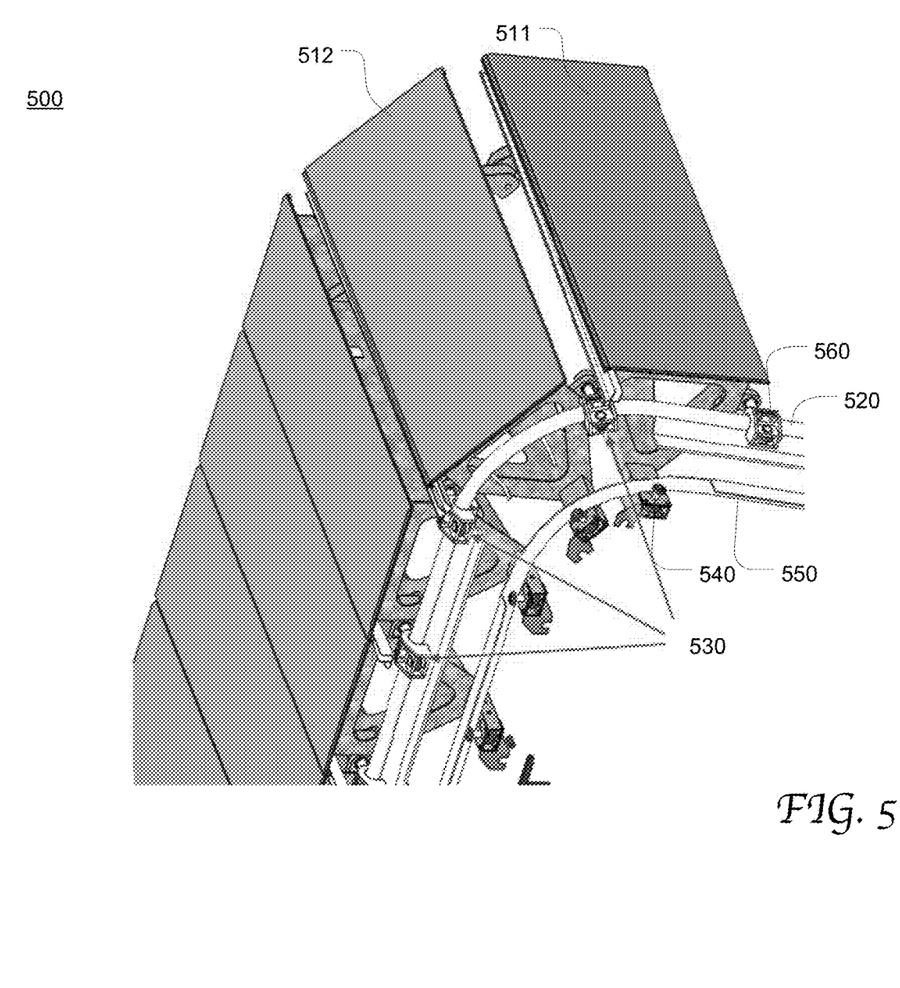
FIG. 5 illustrates the exemplary coupling mechanism between the floor segments and the rail and the exemplary linking mechanism between the floor segments according to an embodiment of the present disclosure.

FIG. 4 illustrates an exemplary floor segment 400 according to an embodiment of the present disclosure. In some embodiments, all the segments in a floor train may be identical, although this implementation is merely exemplary. The floor segment 400 is of a box construction and includes a rectangular top panel 410 and 4 bottom panels 420, 430, 440 and 460 that are all approximately triangular. Several brackets, tabs and fasteners (e.g., 450) are disposed in various locations on the segment 400 and used for coupling the segments together or to other components of the floor system, as shown in FIG. 5. The floor segment 400 is made of folded sheet metal, e.g., aluminum. However, any other suitable material, composition or fabrication may also be used to manufacture a floor segment, such as moulded glass fiber-reinforced plastic (GFRP) or carbon fiber-reinforced plastic (CFRP), GRP over a foam core, frame fabricated from steel sections, and roto-molded plastic, e.g., Polyethylene. The thicknesses of the panels are dictated by the requirement to bear the weight of a person standing at the unsupported far end on the right side of the image.

FIG. 5 illustrates the exemplary coupling mechanism between the floor segments and the rail and the exemplary linking mechanism among the floor segments according to an embodiment of the present disclosure. As shown, the floor segments are coupled to the rail 520 through bogies which have rollers rolling on the rail 520. A bogie 531 is mounted on the pivot between floor segments (e.g., segments 511 and 512) and interconnects the segments. An anti-rotation roller 540 is placed on the lower part of the floor segment and can roll along a secondary rail 550 that is parallel to the rail 520.

Figure 6:
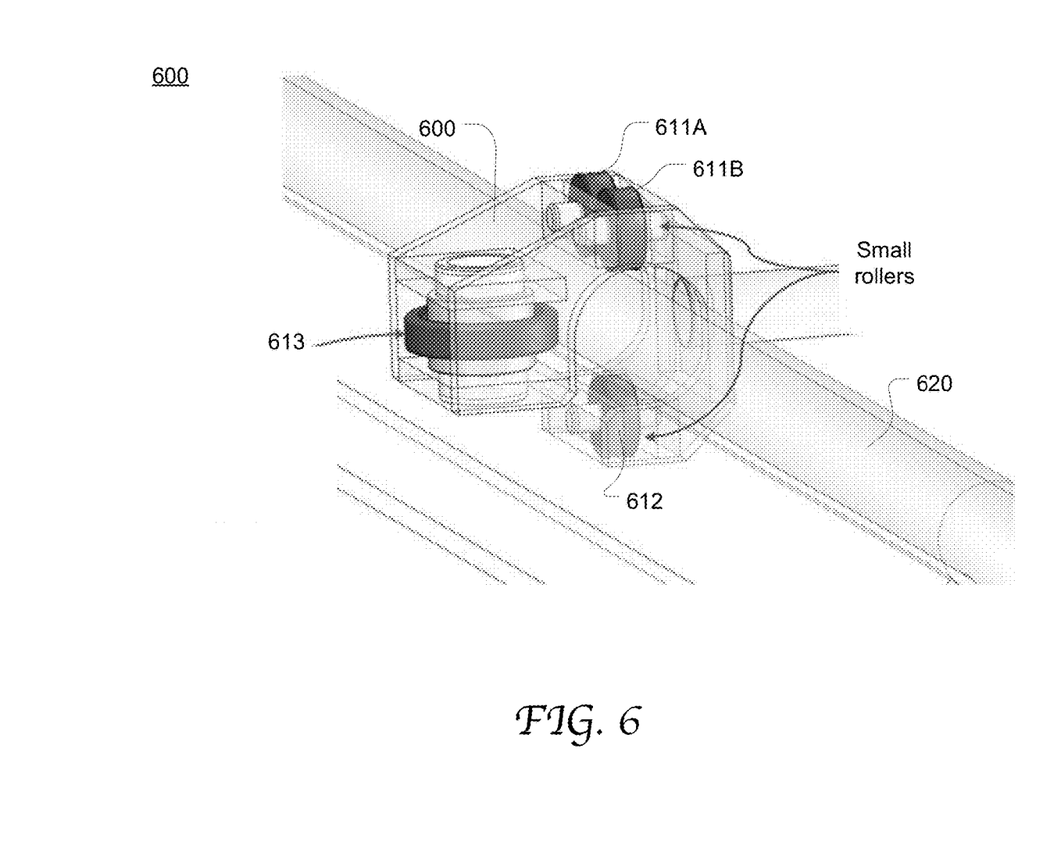
FIG. 6 illustrates an exemplary bogie used for coupling a floor segment to the rail according to an embodiment of the present disclosure.

FIG. 6 illustrates an exemplary bogie 600 used for coupling a floor segment to the rail 620 according to an embodiment of the present disclosure. In this embodiment, Jacobs bogies are used. As Jacobs bogies usually perform better when pushed than traditional bogies, each floor train may be actuated on a single end. Additionally, the resulting system is simpler and requires fewer bearings, as the connection between each segment also serves as the bogie pivot. However, it will be appreciated that any other type of bogies or any other suitable coupling mechanism can also be used to interconnect the floor segments and support their movement of along the rail.

As shown, the bogie 600 have rollers placed at 0° (top), 180° (bottom) and 270° (side). The rollers can resist the loads seen by the floor segments during operation. The loads vary as the floor moves around the track and as the orientation of the associated segment changes. The highest loads are seen when the floor segment is on the upper horizontal section, with the top panel facing upward (see FIG. 11), since the floor has to support people and equipment as well as itself on this section of track. The top rollers 611A and 611B and the side roller 620 are relatively small and can act to resist vertical forces. The side roller 613 is large and capable of resisting large reaction force.

In a floor train, the components (e.g., the bogies) that interface the floor segments to the rail and the chassis may be different among the floor segments. In this example, the leading segment on each train has a unique bogie 560 that allows connections to the drive belt. The leading bogie may be along the top surface of the leading segment. This is important for a simple toothed belt system, as the leading bogie at the top surface never needs to negotiate a corner.

Figure 7:
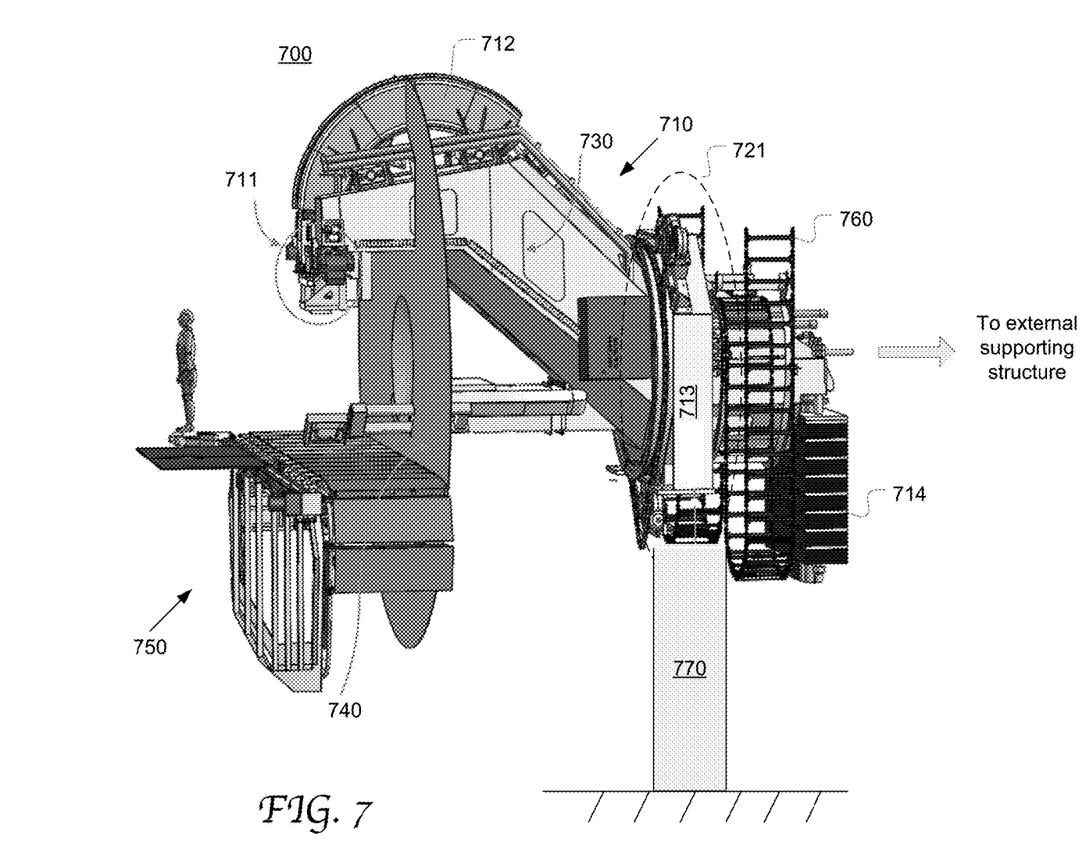
FIG. 7 illustrates the configuration of an exemplary proton beam therapy system including a cantilever gantry and the exemplary moving floor system according to an embodiment of the present disclosure.

A moving floor system according to the present disclosure can be advantageously used in conjunction with a compact cantilever gantry. FIG. 7 illustrates the configuration of an exemplary proton beam therapy system 700 including a cantilever gantry 710 and the exemplary moving floor system 750 according to an embodiment of the present disclosure. The moving floor system 750 and components thereof are similar with the embodiments described above with reference to FIGS. 3A-6.

The cantilever gantry 710 includes a gantry beamline for transporting a proton beam to the beam nozzle 710. A series of magnets in the gantry beamline operate to direct the beam transportation. The proton beam is eventually irradiated onto a patient through the beam nozzle. The cantilever gantry 710 can rotate around an iso-center which defines the positioning of the patient table (not shown) and so a patient for operation.

The gantry beamline may be equipped with a pencil beam scanning nozzle using scanning magnets to control the lateral positions (X and Y) of the beam spot according to a predetermined scanning position (e.g., in spot scanning) or scanning path (e.g., in raster scanning). The gantry beamline also includes the first and the second (final) dipole magnets as the bending magnets, the quadrupole magnets as focusing magnets, and steering and correction magnets for centering the beam in the beamline. Typically, the two dipole magnets bend the proton beam by 90° in total. More specifically, the first dipole magnet (not explicitly shown) is operable to bend the proton beam by an acute angle, e.g., 50°, and the second dipole magnet 712 is operable to bend the proton beam by an obtuse angle, e.g., 140°.

According to the present disclosure, the cantilever gantry 710 is configured as a cantilevered arm having a fixed end portion mounted to an external supporting structure 770 and an open end portion coupled to the beam nozzle 711. More specifically, the weight of the cantilever gantry 200 is supported at one location through the bearing 713. The remainder of the gantry is suspended. The free end portion is coupled to the beam nozzle 711. Thus, compared with a conventional simply-supported gantry, a cantilever gantry according to the present disclosure eliminates the need for a bearing or a roller or other support structure around the treatment area. Thereby random deflection errors caused by misalignment between two supporting rollers are removed. Also, the end-to-end gantry length of a cantilever gantry can be much shorter.

The gantry cover 740 is useful to block users' view into the gantry structures. An energy chain 760 (or cable chain) and a large counterweight 714 are disposed in the fixed end portion. The counterweight 714 acts to keep the system center of mass close to the supporting area (as indicated by the dotted circle 721) of the cantilever gantry 710.

In some embodiments, the external supporting structure is mounted on the ground or a building wall. However, the present disclosure is not limited by the configuration of the external support structure. Nor is it limited by the affixation technique or mechanism used to couple the gantry to an external support structure.

The main bearing 713 is installed in the fixed end portion 721 such that the cantilever gantry 710 can rotate, e.g., covering a full range of 360° or greater. The gantry beamline runs through the interior of the bearing. In this example, the main bearing is coupled to the external supporting structure and also serves to support the weight of the cantilever gantry. However, it will be appreciated that a cantilever gantry can be supported in a range of other suitable locations along the gantry without departing from the scope of the present disclosure.

More specifically, the main bearing 713 may be attached to a base structure embedded into concrete. The weight of the gantry (especially the magnets in the gantry beamline) can be supported by a rigid structure in the gantry e.g., a rigid housing 730 of the gantry. The rigid structure is coupled to the bearing and thus can be rotated. The rigid structure also contains, or is otherwise coupled to, counter weights to reduce tilting moment and required torque to rotate off-set mass of the gantry.

In some example the main bearing 713 is disposed around the first bending magnet or adjacent to one end of it. The main bearing may be a slew bearing sufficiently large to encompass the sweeping volume of the first bending magnet. However, the main bearing may also be implemented in any other suitable technology and configuration without departing from the scope of the present disclosure. Further, in some other embodiments, a rotating mechanical component other than a bearing can be used to enable rotational motion of the cantilever gantry.

Therefore, according to embodiments of the present disclosure, a proton beam gantry is configured as a cantilever arm and its weight is supported in a cantilevered manner from one location, e.g., through the main bearing. The cantilevered gantry is configured to be able to de-couple from the rotating mechanism, advantageously allowing the beam optics geometry to be modified without significantly changing the rotating bearing structure. Further, with the simplified supporting mechanism, a cantilever gantry can be made compact and lightweight, allowing significant flexibility in the positioning of a patient while maintaining the full range rotation capacity. For example, with a cantilevered configuration according to one embodiment of the present disclosure, a gantry that can rotate in 360° is capable of producing a beam footprint that is 10~15% smaller than a conventional gantry.

In some embodiments, a cantilever gantry can be configured and manufactured as a separate system from the beam delivery system (e.g., a beam nozzle) and imaging systems (e.g., used in a positioning verification system). The cantilever gantry is equipped with interface structures with the external beam delivery system and the imaging systems. In this manner, the beam optics can be changed without changing the rotating mechanical structure. Also, replacement of magnets, main structure, and main bearing can be performed in the field without being sent back to manufacturing. However, in some other embodiments, a beam delivery system and imaging systems are integral parts of a cantilever gantry. In some embodiments, the two floor segments on either side of the beam nozzle have windows that allow imaging X-ray to pass.

Most conventional 360° gantries are assembled on-site, requiring the beamline to be fitted and aligned while the gantry is constructed. A significant number of cables and equipment are fitted on-site, leading to variations in installation quality and duration as well as very high installation cost. According to the present disclosure, a cantilever gantry may be manufactured and delivered to a health care facility as a fully-assembled, pre-tested unit, with the beamline factory-assembled and aligned, as well as the beam nozzle, all the cables, vacuum and plumbing systems, motor brakes, rotation drive mechanisms, media chains, imaging devices, and etc. It will be appreciated that a cantilever gantry according to the present disclosure may include a wide range of components that are well known in the art, such as energy selection system (ESS) with an energy degrader, an in-situ beam diagnostic mechanism used to monitor beam position and beam current, and etc.

Figure 8:
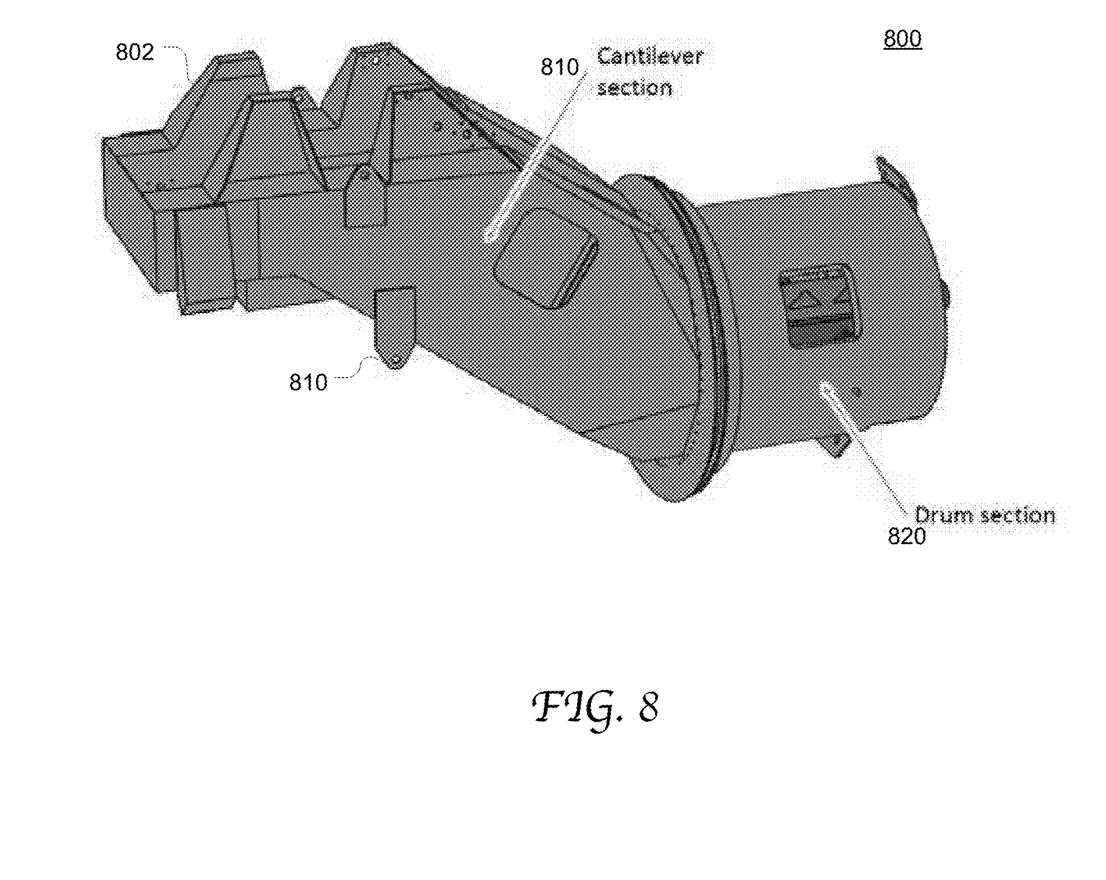
FIG. 8 illustrates an exemplary monocoque housing 800 in a cantilever gantry according to an embodiment of the present disclosure.

In some embodiments, a cantilever gantry includes a monocoque or fully integrated box structure used as the frame or exterior housing. The present disclosure is not limited by the material compositions, configuration or geometry of monocoque housing of a cantilever gantry. For example, a monocoque housing can be made of Aluminum, carbon fiber, steel, a composite material or etc. FIG. 8 illustrates an exemplary monocoque housing 800 in a cantilever gantry according to an embodiment of the present disclosure.

The monocoque housing 800 may be fully welded and includes a cantilever section 810 and a drum section 820. Alternatively, the two sections may be separate monocoque parts and coupled together through another coupling mechanism. The main bearing may be disposed at the joint area of the two sections. Each section of the monocoque housing may be a fully welded steel monocoque or box structure. The cantilever section 810 may contain the gantry beamline starting after the first bending magnets and the associated components. A nozzle may be coupled to, or enclosed in, the open end of the cantilever section 810 that extends over the treatment room. An imaging system may also be mounted to the cantilever section 810. The drum section 820 is substantially cylindrical and may enclose, or otherwise is coupled with, the main bearing, the signal and power cables, the beamline up to the first bending magnet, vacuum and plumbing components, emergency motor brakes, rotation drive mechanisms, the counterweight, media chains and/or imaging devices. The monocoque housing 800 includes protrusions or other features formed to fit the various components of the gantry.

The cantilever section 810 may be constructed of welded steel plates which form the load-carrying outer skin. The cantilever section 810 may be made increasingly stiffer toward the main bearing location to counter the significant forces imposed in this region. In some embodiments, the base (fixed end portion) of the cantilever gantry is stiffened by increasing the plate thickness near the main bearing. The drum section 820 can be constructed from a heavy wall steel tube.

Monocoque housing in a gantry advantageously provides superior stiffness-weight ratio, particularly for torsional load created by the heavy second bending dipole when the gantry rotates to the ±90° positions. The cantilever section 810 may have a generally tapered shape in various directions, with its open end much narrower than the joint end. This can help maintain stiffness of the gantry through all angles of rotation.

Moreover, by using monocoque housing, a gantry according to the present disclosures can be delivered to a health care facility as a fully-assembly, pre-tested unit. Consequently, the expenditure associated with manufacturing, transportation, installation, assembling and maintenance can be dramatically and advantageously decreased.

Figure 9:
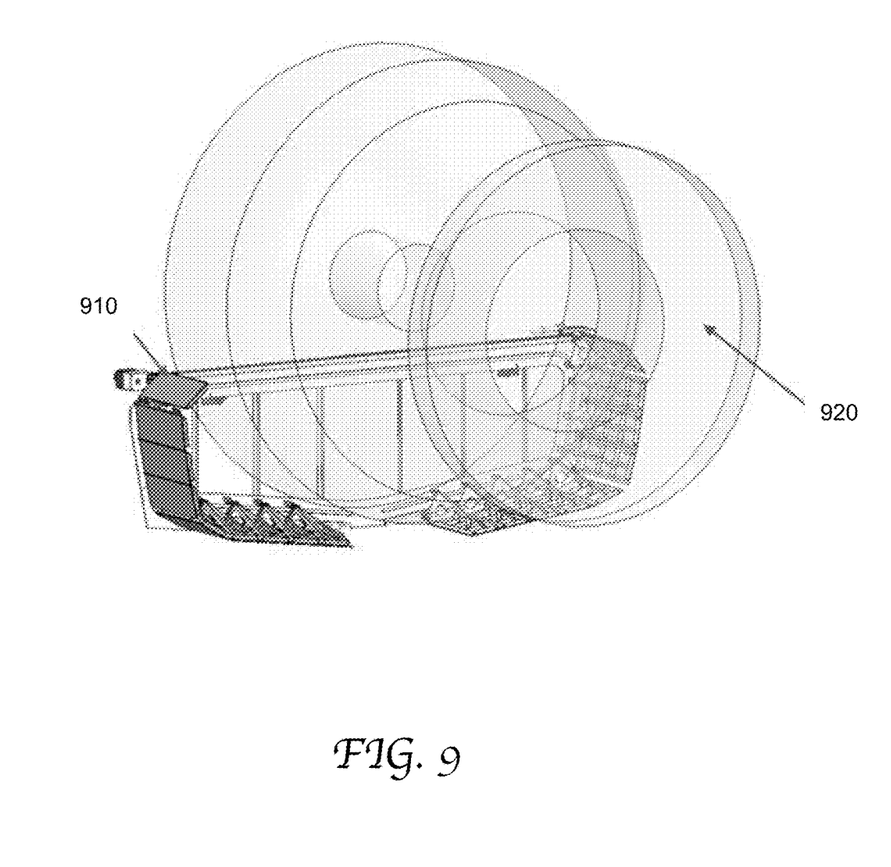
FIG. 9 illustrates an inoperable state of an exemplary moving floor system in relation to the gantry sweep according to an embodiment of the present disclosure.

A moving floor system according to the present disclosure may include an emergence brake to prevent the floor moving, e.g., in the event of a drive belt breaking. The emergency brake may be over-ridable, allowing the floor to be manually moved out of the way of the gantry and thereby allowing treatment to continue. FIG. 9 illustrates an inoperable state of an exemplary moving floor system 910 in relation to the cantilever gantry sweep 920 according to an embodiment of the present disclosure. In this state, the motor drive and brakes are disengaged and the floor has dropped under gravity to its park position. Thus, the floor trains are moved to, and parks at, a "home" position outside of the gantry sweep 920 so they do not impede the motion of the cantilever gantry.

Figure 10A:
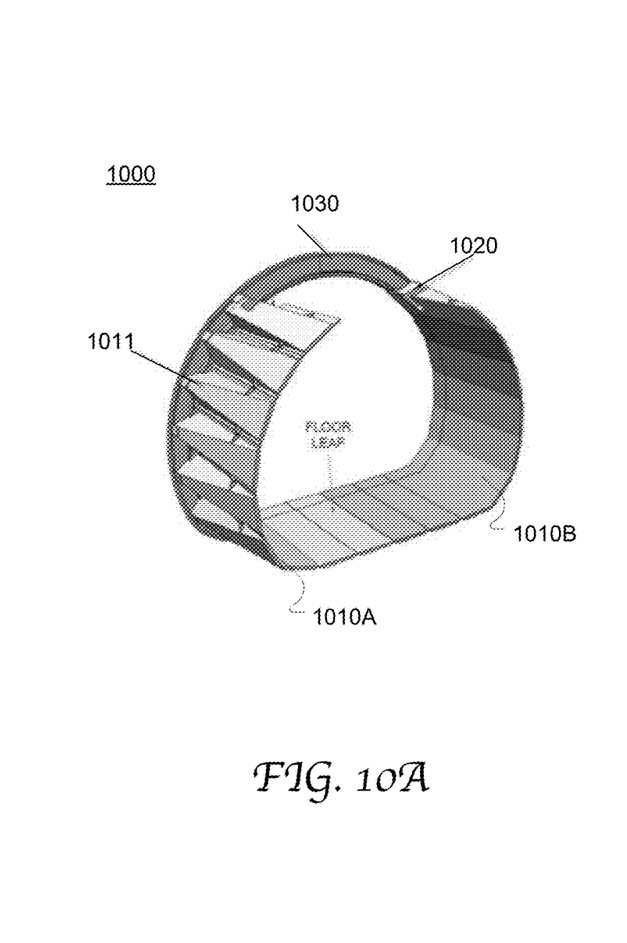
FIG. 10A illustrates the configuration of an exemplary moving floor system with the floor excess rolling up according to a third embodiment of the present disclosure.
Figure 10B:
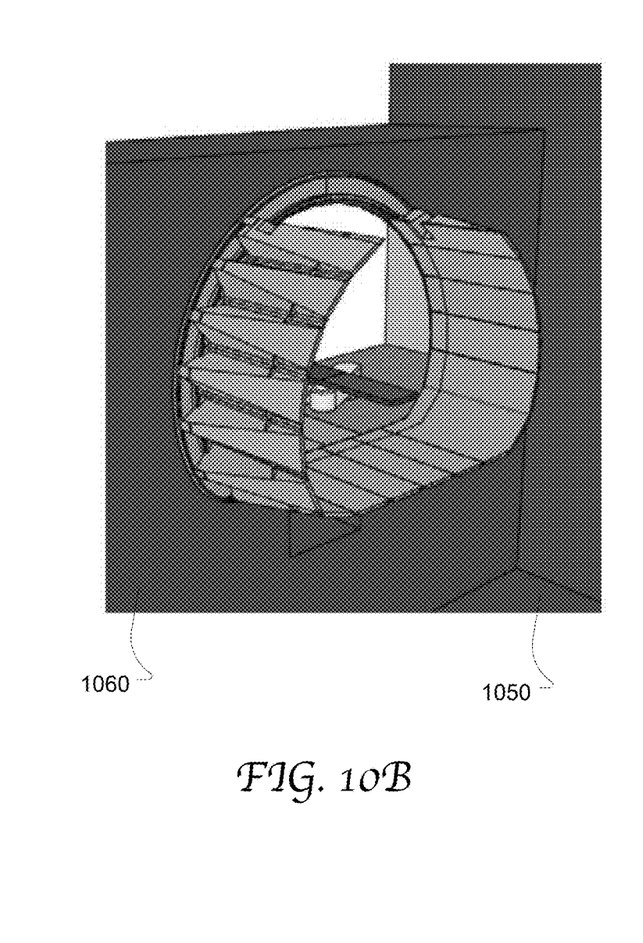
FIG. 10B illustrates the exemplary moving floor system installed on the bunker wall according to the third embodiment of the present disclosure.

FIG. 10A illustrates the configuration of an exemplary moving floor system with the floor excess rolling up according to a third embodiment of the present disclosure. FIG. 10B illustrates the exemplary moving floor system mounted on the bunker wall according to the third embodiment of the present disclosure. In this example, the track 1030 is a "D"-like shaped closed continuous loop where the non-lateral portions of the track curve up and disposed above the floor plane. However, the track may be implemented in any other suitable shape without departing from the scope of the present disclosure, such as rectangular. In some other embodiments, the floor system 1000 can be similarly used in conjunction with a cantilever gantry system as described in greater detail with reference to FIG. 7. However, the present disclosure is not limited to any specific type of gantry system.

The floor system 1000 includes a flexible floor configured to move along the single track 1030. The track 1030 with a rail, the floor trains 1010A and 1010B composed of floor segments (e.g., 1011), the bogies, the drive system, the brake system, and etc., can be implemented similarly with the other embodiments as described above with reference to FIGS. 1A-9. Depending on the geometries of the gantry and nozzle and track, this can function with just a single floor train.

During rotation of the cantilever gantry and viewed in the treatment area, when the beam nozzle is positioned above the patient table, the floor moves and maintains a continuous surface; when the beam nozzle is directed to the side or under the patient table, an opening is maintained in the floor through which the beam nozzle protrudes. The opening follows the changing positions of the beam nozzle and moves in the floor plane in synchronization with the rotation of the gantry. Different from the embodiments with a curving down track, as the floor segments move along the curving-up track, they can move above the floor plane and may be visible in the treatment area, e.g., create an alcove as illustrated.

In some embodiments, the two floor trains separate when the beam nozzle is traversing the lateral portion of the track trail, creating a gap at the top of the treatment area. This occurs because as the gantry rotates, the length of the track 1030 that is exposed by the gantry/nozzle changes. This gap can be filled by a solid cover protruding from the rear wall of the treatment station. By making the track 1030 approximately 'D' shaped, this gap is never underfoot.

Each floor segment is mounted on the track 1030 on only one side and thus supported in a cantilevered manner. During system down time, the two floor trains 1010A and 1010B provide a stationary and continuous floor on which a clinician can stand. During operation while the gantry rotates in a range that requires no interplay between the gantry and the floor, the ends of the two floor trains 1010A and 1010B meet and present a continuous floor to cover the bunker pit 1050 that otherwise would be undesirably exposed to a patient. In this situation, the flexible floor may moves along the track 1030.

In some embodiments, the "D" shaped formed by the two floor trains 1010A and 1010B is entirely within the sweep of the gantry, and there is always an opening for the beam nozzle to protrude from. However in some other embodiments, when the gantry rotates in a range where at least a portion of the gantry is below the floor plane, the two floor trains are separated to create an opening in the floor for the beam nozzle to pass through. The present disclosure is not limited to any specific angular position of the gantry from which the floor starts to open and allows the gantry to enter. Such angular position varies in different embodiments depending on the particular physical configurations of the gantry and the nozzle.

As the gantry rotates further under the floor plane, the opening consistently follows the varying position of the beam nozzle. Further, the dimension of the opening may dynamically vary with position of the beam nozzle. As a result, the beam nozzle and the floor trains 1010A and 1010 B in combination can form an effective moving cover of the bunker pit 1050. It will be appreciated that the present disclosure is not limited by the particular portion of the beam nozzle and/or gantry that can protrude above the opening.

In some embodiments, a single floor train is used and the opening is formed between the two ends of the floor train. Two hinged flaps may be disposed between the nozzle and the nearest edges of the floor train to accommodate variation in the opening size, especially if the variation can be kept small.

In this embodiment, the non-lateral portions of the track 1030 are substantially vertical and bent upward from the ends of the bottom lateral portion. Thus, the floor excess segments can roll along the non-lateral portions upward and thus may be visible in the treatment area.

The two floor trains 1010A and 1010B may be independently driven by separate motors and coupled to separate brakes, allowing them to travel along the track at different speeds and in different directions. The motors are controlled to enable the floor trains to move in synchrony with gantry rotation and thereby to dynamically adjust the dimension and position of the opening for the beam nozzle to pass through. In some other embodiments, the floor trains 1010A and 1010B may be passively driven by motion of the gantry and the beam. nozzle.

In the illustrated example, the curving-up track 1030 is mounted on the concrete of the wall of the treatment station. However, in some other embodiments, the track and the floor trains can be mounted onto a steel chassis plate, enabling the entire floor system to be a standalone pre-assembled module. The chassis and various components integrated thereon may be implemented in similar configurations with the other embodiments as described in greater detail with reference to FIGS. 3A-6. The floor trains, individual floor segments, and the mechanisms of coupling to the track rail and interconnecting the floor segments can be implemented in similar configurations with the other embodiments as described above in greater detail with reference to FIGS. 4-6.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A radiotherapy system comprising:
   an accelerator configured to provide a particle beam with an initial energy;
   a support member operable to be coupled to an external supporting structure;
   a cantilever gantry assembly coupled to said accelerator and said support member and comprising a gantry beamline configured to transport said particle beam, wherein said cantilever gantry assembly is configured to be supported by said support member in a cantilevered manner;
   a beam nozzle coupled to said cantilever gantry assembly and configured to irradiate said particle beam onto a target object;
   a moving floor configured to:
      support a person;
      move in a lateral plane in synchronization with rotation of said cantilever gantry assembly and perpendicular to a rotation axis of said cantilever gantry assembly; and
      during movement in said lateral plane, maintain an opening that allows said beam nozzle to protrude therefrom and toward said target object when said cantilever gantry assembly is located below said lateral plane during rotation; and
   a track configured to be affixed to an external wall and to support the moving floor, wherein said track comprises a continuous rail comprising a lateral portion configured to guide said moving floor to move in said lateral plane,
   wherein the moving floor comprises two floor sections each configured to move in said lateral plane, and wherein further said opening is variable and corresponds to a gap between said two floor sections, and wherein each floor section comprises a plurality of floor segments interconnected in sequence by bogies, and wherein further each of said plurality of floor segments is configured to be supported by said continuous rail in a cantilevered manner through said bogies.

2. The radiotherapy system of claim 1, wherein said continuous rail further comprises a non-lateral portion bent upward from said lateral portion and configured to guide said moving floor to move above said lateral plane.

3. The radiotherapy system of claim 1, wherein said continuous rail further comprises a non-lateral portion bent downward from said lateral portion and configured to guide said moving floor to move below said lateral plane.

4. The radiotherapy system of claim 1, wherein each bogie is mounted on a pivot between floor segments wherein said bogie comprises rollers disposed on an outer surface of said continuous rail in three different angles, and wherein further said rail is a tubular rail.

5. The radiotherapy system of claim 1 further comprising a respective drive motor and a respective brake that are coupled to said track and configured to control each floor section.

6. The radiotherapy system of claim 1, wherein said support member comprises a bearing configured to enable said cantilever gantry assembly to rotate around an isocenter of said radiotherapy system in a range between −190° and 190°.

7. The radiotherapy system of claim 1 further comprising a counterweight coupled to said cantilever gantry assembly and disposed proximate to said support member, wherein said cantilever gantry assembly comprises a rigid housing configured to support a weight of said cantilever gantry assembly.

* * * * *